United States Patent [19]

Lesher et al.

[11] 4,361,568

[45] * Nov. 30, 1982

[54] 5-(PYRIDINYL)-1H-PYRAZOLO[3,4-B]PYRIDIN-3-AMINES AND THEIR CARDIOTONIC USE

[75] Inventors: George Y. Lesher, Schodack; Monte D. Gruett, Greenbush, both of N.Y.

[73] Assignee: Sterling Drug Inc., New York, N.Y.

[*] Notice: The portion of the term of this patent subsequent to Apr. 28, 1998, has been disclaimed.

[21] Appl. No.: 258,363

[22] Filed: Apr. 28, 1981

[51] Int. Cl.$^3$ .................... A61K 31/44; C07D 471/04
[52] U.S. Cl. ..................................... 424/263; 546/119
[58] Field of Search ......................... 546/119; 424/263

[56] References Cited

U.S. PATENT DOCUMENTS 3,872,133  3/1975  Fleckenstein et al. ............... 546/119
4,264,603  4/1981  Lesher et al. ......................... 546/119
4,265,895  5/1981  Lesher et al. ......................... 546/119

OTHER PUBLICATIONS

Hoehn, Chem. Abst., 1973, vol. 78, No. 84404f.
Vercek et al., J. Org. Chem., 1979, vol. 44(10), pp. 1695–1699.
Balicki et al., Chem. Abst., 1977, vol. 87, No. 39357t.
Chemical Abstracts, vol. 87, item 39,357t, 1977.
Balicki et al., Acta Pol. Pharm. 1976, 33(3), 289–293, (Pol.).

*Primary Examiner*—Henry R. Jiles
*Assistant Examiner*—Natalia Harkaway
*Attorney, Agent, or Firm*—Robert K. Bair; B. Woodrow Wyatt; Paul E. Dupont

[57] ABSTRACT

1-R-3-(NB)-5-PY-6-Q-1H-pyrazolo[3,4-b]pyridines or pharmaceutically-acceptable acid-addition salts thereof, which are useful as cardiotonics, are prepared by reacting a 1-R-5-PY-6-Q-1H-pyrazolo[3,4-b]pyridin-3-amine with a lower-alkanoic acid and reducing agent to produce 1-R-3-(NB)-5-PY-6-Q-1H-pyrazolo[3,4-b]pyridine (I) where NB is NHR$_1$ or NR$_1$R$_2$, with a mixture of formic acid and formaldehyde to produce I where NB is N(CH$_3$)$_2$ or with a lower-acylating agent to produce I where NB is NHAc and, if desired, reacting the 3-(NHAc) compound with a reducing agent to prepare the corresponding 3-NHR$_1$ compound, where R is lower-alkyl, lower-hydroxyalkyl, lower-acyloxy-(lower-alkyl) or lower-alkoxy-alkyl, Q is hydrogen or lower-alkyl, PY is 4- or 3-pyridinyl or 4- or 3-pyridinyl having one or two lower-alkyl substituents, and NB is selected from NHR$_1$, NR$_1$R$_2$ or NHAc where R$_1$ and R$_2$ are each lower-alkyl and Ac is lower-acyl. Also shown are cardiotonic compositions and method for increasing cardiac contractility using said compounds or salts.

14 Claims, No Drawings

5-(PYRIDINYL)-1H-PYRAZOLO[3,4-B]PYRIDIN-3-AMINES AND THEIR CARDIOTONIC USE

CROSS-REFERENCE TO RELATED APPLICATIONS

The 1-R-5-PY-6-Q-1H-pyrazolo[3,4-b]pyridine-3-amines used herein as intermediates are disclosed and claimed in copending application Ser. No. 131,227, filed Mar. 17, 1980 and now U.S. Pat. No. 4,264,603, issued Apr. 28, 1981.

The 1,2-dihydro-2-oxo-5-(pyridinyl)-6-(lower-alkyl) nicotinonitriles disclosed herein as intermediates are disclosed and claimed as cardiotonics and as intermediates in copending U.S. patent application Ser. No. 198,461, filed Oct. 20, 1980 and now U.S. Pat. No. 4,313,951, issued Feb. 2, 1982, a continuation-in-part of application Ser. No. 97,504, filed Nov. 26, 1979 and now abandoned.

BACKGROUND OF THE INVENTION (a) Field of the Invention

This invention relates to pyrazolo[3,4-b]pyridin-3-amines, their preparation and their use as cardiotonics.

(b) Description of the Prior Art

Chemical Abstracts Vol. 87, item 39,357t, 1977, reads as follows:

"Dipyridyls. VII. Reaction of β-ketoaldehydes with cyanoacetic acid hydrazide. Balicki, Roman; Kaczmarek, Lukasz; Nantka-Namirski, Pawel (Inst. Org. Chem., Pol. Acad. Sci., Warsaw, Pol.). Acta Pol. Pharm. 1976, 33(3), 289–93 (Pol.). $RCOCH_2CHO$ (R=Me, Ph, 3- and 4-pyridyl, and

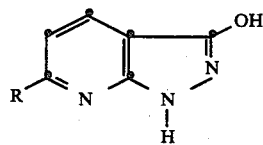

6-methyl-3-pyridyl) condensed in an alka. medium with $NCCH_2CONHNH_2$ (I) to give the pyrazolopyridines II. II were also obtained when 5-amino-3-pyrazolone was used instead of I. II (R=3- and 4-pyridyl) were also preped. in the reaction of Me 6-(3- and 4-pyridyl)-2-chloro-3-cyanopyridines with 80% $NH_2NH_2.H_2O$."

The original article (p. 291) shows that the compounds of formula II (supra) can also exist in tautomeric 1,2-dihydro-6-R-2H-pyrazolo[3,4-b]pyridin-3-one form.

SUMMARY OF THE INVENTION

In a composition of matter aspect, the invention resides in 1-R-3-(NB)-5-PY-6-Q-1H-pyrazolo[3,4-b]pyridines or pharmaceutically-acceptable acid-addition salt thereof, where R, NB, PY and Q are defined hereinbelow, which are useful as cardiotonic agents.

A composition aspect of the invention resides in a cardiotonic composition for increasing contractility in a patient, said composition comprising a pharmaceutically-acceptable carrier and, as the active ingredient thereof, a cardiotonically-effective amount of 1-R-3-(NB)-5-PY-6-Q-1H-pyrazolo[3,4-b]pyridines or pharmaceutically-acceptable acid-addition salt thereof.

In a method aspect, the invention resides in a method for increasing cardiac contractility in a patient requiring such treatment which comprises the administration of a medicament comprising a pharmaceutically-acceptable carrier and, as the active component, thereof, a cardiotonically-effective amount of 1-R-3-(NB)-5-PY-6-Q-1H-pyrazolo[3,4-b]pyridine or pharmaceutically-acceptable acid-addition salt thereof.

The invention in another process aspect comprises reductively alkylating a 1-R-5-PY-6-Q-1H-pyrazolo[3,4-b]pyridin-3-amine with a lower-alkanoic acid and reducing agent to produce a 1-R-3-($NHR_1$ or $NR_1R_2$)-5-PY-6-Q-1H-pyrazolo[3,4-b]pyridine (I) where R, $R_1$, $R_2$, PY and Q have the meanings given below. An alternative process aspect for preparing said compound (I) where $NR_1R_2$ is $N(CH_3)_2$ comprises reacting 1-R-5-PY-6-Q-1H-pyrazolo[3,4-b]pyridin-3-amine with a mixture of formic acid and formaldehyde.

The invention in another process aspect comprises alkylating with a lower-acylating agent a 1-R-5-PY-6-Q-1H-pyrazolo[3,4-b]pyridin-3-amine to produce a 1-R-3-(NHAc)-5-PY-6-Q-1H-pyrazolo[3,4-b]pyridine where R, PY, Q and Ac have the meanings given below.

Another process aspect of the invention comprises reacting a 1-R-3-(NHAc)-5-PY-6-Q-1H-pyrazolo[3,4-b]pyridine with a reducing agent capable of reducing lower-alkanoylamino to lower-alkylamino to produce a 1-R-3-($NHR_1$)-5-PY-6-Q-1H-pyrazolo[3,4-b]pyridine where R, $R_1$, Ac, PY and Q have the meanings given below.

DETAILED DESCRIPTION INCLUSIVE OF PREFERRED EMBODIMENTS

In a composition of matter aspect the invention resides in a 1-R-3-(NB)-5-PY-6-Q-1H-pyrazolo[3,4-b]pyridine having formula I

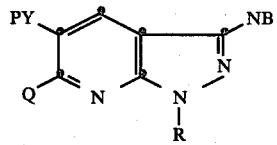

where R is lower-alkyl, lower-hydroxyalkyl, lower-acyloxy(lower-alkyl) or lower-alkoxyalkyl, Q is hydrogen or lower-alkyl, PY is 4-or 3-pyridinyl or 4- or 3-pyridinyl having one or two lower-alkyl substituents, and NB is selected from $NHR_1$, $NR_1R_2$ or NHAc where $R_1$ and $R_2$ are each lower-alkyl and Ac is lower-alkanoyl or pharmaceutically-acceptable acid-addition salt thereof. The compounds of formula I are useful as cardiotonic agents, as determined by standard pharmacological evaluation procedures. The compounds of formula I where NB is NHAc also are useful as intermediates in preparing the compounds of formula I where NB is $NHR_1$. Preferred embodiments are those of formula I where PY is 4-pyridinyl or 3-pyridinyl, R is methyl, ethyl, 2-hydroxyethyl, 2-hydroxypropyl, 2-formyloxyethyl or 2-acetyloxyethyl, Q is hydrogen, methyl or ethyl, and NB is $NHCH_3$, $N(CH_3)_2$, $NHC_2H_5$, NHCHO or $NHCOCH_3$. Particularly preferred embodiments are the compounds of formula I where R is methyl, ethyl, 2-hydroxyethyl or 2-hydroxypropyl, Q is hydrogen or methyl, PY is 4-pyridinyl and NB is $NHCH_3$, $NHC_2H_5$ or $N(CH_3)_2$, or pharmaceutically-acceptable acid-addition salt thereof.

A composition aspect of the invention resides in a cardiotonic composition for increasing cardiac contractility, said composition comprising a pharmaceutically-acceptable carrier and, as the active component thereof, a cardiotonically-effective amount of 1-R-3-(NB)-5-PY-6-Q-1H-pyrazolo[3,4-b]pyridine of formula I, where R, NB, PY and Q are each defined as in formula I, or pharmaceutically-acceptable acid-addition salt thereof. Preferred embodiments are those having as active components the above-said preferred embodiments of formula I.

A method aspect of the invention resides in the method for increasing cardiac contractility in a patient requiring such treatment which comprises administering orally or parenterally in a solid or liquid dosage form to such patient said cardiotonic composition comprising a pharmaceutically-acceptable carrier and, as the active component thereof, a cardiotonically-effective amount of 1-R-3-(NB)-5-PY-6-Q-1H-pyrazolo[3,4-b]pyridine of formula I where PY, R, Q and NB are defined as in formula I, or pharmaceutically-acceptable acid-addition salt thereof.

In a process aspect the invention resides in the process which comprises reacting a 1-R-5-PY-6-Q-1H-pyrazolo[3,4-b]pyridin-3-amine with a lower-alkanoic acid and reducing agent to produce the 1-R-3-(NB)-5-PY-6-Q-1H-pyrazolo[3,4-b]pyridine where NB is $NHR_1$ or $NR_1R_2$ and $R_1,R_2$, R, PY and Q have the meanings given above for formula I. An alternative process aspect of the invention for preparing the compounds of formula I where $NR_1R_2$ is $N(CH_3)_2$ comprises reacting 1-R-5-PY-6-1H-pyrazolo[3,4-b]pyridin-3-amine with a mixture of formic acid and formaldehyde.

In another process aspect the invention resides in the process which comprises reacting a 1-R-5-PY-6-Q-1H-pyrazolo[3,4-b]pyridin-3-amine with a lower-acylating agent to produce the 1-R-3-(NHAc)-5-PY-6-Q-1H-pyrazolo[3,4-b]pyridine where R, Ac, PY and Q have the meanings given for formula I and, where desired, reacting said 1-R-3-(NHAc)-5-PY-6-Q-1H-pyrazolo[3,4-b]pyridine with a reducing agent capable of converting lower-alkanoyl amino to lower-alkylamino to produce the 1-R-3-(NHR$_1$)-5-PY-6-Q-1H-pyrazolo[3,4-b]pyridine of formula I where R, $R_1$, PY and Q have the meanings given for formula I.

The term "lower-alkyl" as used herein, e.g., as one of the meanings for R or Q or as a substituent for PY or as $R_1$ or $R_2$ in formula I, means alkyl radicals having from one to six carbon atoms, that is, 1 to 6 C's which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of PY in formula I where PY is 4- or 3-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-hydroxyalkyl" as used herein, e.g., for one of the meanings for R in formula I, means hydroxy-alkyl radicals having from two to six carbon atoms, i.e., 2 to 6 C's which can be arranged as straight or branched chains and at least two carbon atoms of which separate hydroxy and the 1-ring nitrogen atom of the pyrazolo[3,4-b]pyridine ring, illustrated by 2-hydroxyethyl, 3-hydroxypropyl, 2-hydroxypropyl, 4-hydroxybutyl, 3-hydroxybutyl, 5-hydroxyamyl, 6-hydroxyhexyl, and the like.

The term "lower-alkanoyl", as used herein, e.g., as the meanings for Ac in formula I, means alkanoyl radicals having from one to six carbon atoms, including straight- and branch-chained radicals, illustrated by formyl, acetyl, propionyl (n-propanoyl), butyryl (n-butanoyl), isobutyryl (2-methyl-n-propanoyl), n-pentanoyl, n-hexanoyl, and the like.

The term "lower-alkoxyalkyl" as used herein, e.g., for one of the meanings for R in formula I, means alkoxyalkyl radicals having from three to six carbon atoms, i.e., 3 to 6 C's, which can be arranged as straight or branched chains and at least two carbon atoms of which separate the oxygen atom of alkoxyalkyl and the 1-ring nitrogen atom of the pyrazolo[3,4-b]pyridine ring, illustrated by 2-methoxyethyl, 2-ethoxyethyl, 3-methoxypropyl, 2-methoxypropyl, 2-methoxybutyl, 4-ethoxybutyl, 3-ethoxypropyl, 3-n-propoxypropyl, and the like.

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form; however, appropriate pharmaceutically-acceptable salts within the scope of the invention are those derived from mineral acids such as hydrochloric acid, hydrobromic acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, guinic acid, and the like, giving the hydrochloride, hydrobromide, sulfate, phosphate, sulfamate, acetate, citrate, lactate, tartrate, methanesulfonate, ethanesulfonate, benzenesulfonate, cyclohexylsulfamate and quinate, respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I) are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structure of the compound of formula I was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutically chemistry to make and use the same, as follows.

The conversion of 1-R-5-PY-6-Q-1H-pyrazolo[3,4-b]pyridin-3-amine to the corresponding 3-NHR$_1$ or 3-NR$_1$R$_2$ derivative (I) is carried out by reacting the 3-amine with a mixture of a lower-alkanoic acid and appropriate reducing agent. An alternative and preferred process for preparing the 3-N(CH$_3$)$_2$ compound is carried out by reacting said 3-amine with a mixture of two or more molar eqivalents each of formic acid and formaldehyde to effect dimethylation of the 3-amino group. This reaction is conveniently run by refluxing said 3-amine with an excess of each of formic acid and formaldehyde, preferably an aqueous solution thereof, preferably more than a two-fold molar excess of each. A convenient means of preparing the 3-NR$_1$R$_2$ compounds (I) is carried out by reacting said 3-amine with an excess each of a lower-alkanoic acid and sodium borohydride, preferably by heating the reactants at about 60° C. to 125° C., preferably about 70° C. to 100° C. The corresponding 3-NHR$_1$ compound can be obtained using molar equivalent quantities of the 3-amine, lower-alkanoic acid and sodium borohydride, preferably at a lower temperature e.g., about 10° C. to 30° C. Also, the compound of formula I where NB is NHR$_1$ can be reacted as above with a lower-alkanoic acid and appropriate reducing agent to produce the compound of formula I where NB is NR$_1$R$_2$ with R$_1$ and R$_2$ being the same or different lower-alkyl groups.

The reaction of 1-R-5-PY-6-Q-1H-pyrazolo[3,4-b]pyridin-3-amine with lower-acylating agent to produce the corresponding 3-NHAc compound (I) is carried out by reacting the 3-amine with a lower-acyl anhydride, acid or acid halide in the presence of an acid-acceptor where necessary. Preparation of the 3-NHCHO compound is conveniently run by heating the 3-amine with formic acid on a steam bath. Preparation of other 3-NH-acyl compounds is conveniently carried out by reacting an excess of a lower-acyl anhydride with the amine in an inert organic base, e.g., pyridine, which acts as acid-acceptor. Where the 3-amine has a 1-(lower-hydroxyalkyl) substituent, the resulting 3-NHAc compound has a 1-(lower-acyloxy)(lower-alkyl) substituent; selective acylation of the 3-amine can be achieved using molar equivalent quantities of the 3-amine and lower-acylating agent leaving 1-(lower-hydroxyalkyl) unacylated.

The conversion of the 3-NHAc compounds where Ac is lower-alkanoyl to the corresponding 3-NHR$_1$ compounds is carried out by reacting the 3-NHAc compound with a reagent capable of converting lower-alkanoylamino to lower-alkylamino. This reaction is carried by reacting the 3-NHAc compound with lithium aluminum hydride at about 25° C. to 100° C., preferably about 50° C. to 100° C., preferably using a suitable inert solvent, e.g., tetrahydrofuran, diethylene glycol dimethyl ether (diglyme), and the like.

The preparation of the intermediate of 1-R-5-PY-6-Q-1H-pyrazolo[3,4-b]pyridin-3-amine is carried out by reacting 2-halo-5-PY-6-Q-nicotinonitrile with 1-R-hydrazine by heating the reactants in a suitable solvent at about 50° C. to 100° C., preferably about 65° C. to 85° C., where R, PY and Q have the meanings given above for formula I and halo is chloro or bromo, preferably chloro. The reaction is conveniently run by refluxing the reactants in a lower-alkanol, preferably methanol or ethanol. Other suitable solvents include isopropyl alcohol, dioxane, tetrahydrofuran, dimethylformamide, and the like.

The intermediate 2-halo-5-PY-6-Q-nictotinonitrile is readily prepared by reacting a 1,2-dihydro-2-oxo-5-PY-6-Q-nicotinonitrile with an inorganic halogenating agent preferably by heating the 2-oxo-nicotinonitrile with excess phosphorus oxychloride, conveniently run at reflux temperature (about 107° C.), using a catalytic or small quantity of dimethylformamide. Optionally, a greater quantity of dimethylformamide can be used as solvent; other suitable inert aprotic solvents also can be used, e.g., acetonitrile, dioxane, tetrahydrofuran, and the like. Other suitable inorganic halogenating agents include PCl$_3$, PCl$_5$, PBr$_3$, and the like.

The preparation of known 1,2-dihydro-2-oxo-5-PY-nicotinonitriles is shown in Lesher and Opalka U.S. Pat. No. 4,004,012, issued Jan. 18, 1977.

The preparation of 1,2-dihydro-2-oxo-5-PY-6-(lower-alkyl)nicotinonitriles, which are disclosed and claimed in said copending U.S. patent application Ser. No. 198,461, is described generally in the following three paragraphs and is illustrated further hereinbelow in Examples C-1 through C-11 and D-1 through D-11.

The preparation of 1-PY-2-(dimethylamino)ethenyl lower-alkyl ketone by reacting PY-methyl lower-alkyl ketone with dimethylformamide di-(lower-alkyl)acetal is carried out by mixing the reactants in the presence or absence of a suitable solvent. The reaction is conveniently run at room temperature, i.e., about 20°–25° C., or by warming the reactants up to about 100° C., preferably in an aprotic solvent, conveniently hexamethylphosphoramide because of the method used to prepare the PY-methyl lower-alkyl ketone, as noted below in Example C-1. Other suitable solvents include tetrahydrofuran, dimethylformamide, acetonitrile, ether, benzene, dioxane, and the like. Also, the reaction can be run using no solvent, preferably using an excess of dimethylformamide di-(lower-alkyl)acetal.

The intermediate PY-methyl lower-alkyl ketones are generally known compounds which are prepared by known methods [e.g., as given in Rec. trav. chim 72, 522 (1953); U.S. Pat. No. 3,133,077 (May 12, 1964); Bull. Soc. Chim. France 1968, 4132; Chem. Abstrs. 79, 8539h (1973); Chem. Abstrs. 81, 120,401a (1974); J. Org. Chem. 39, 3834 (1974); Chem. Abstrs. 87, 6594q (1977); J. Org. Chem. 43, 2286 (1978)].

The reaction of 1-PY-2-(dimethylamino)ethenyl lower-alkyl ketone with α-cyanoacetamide to produce 1,2-dihydro-2-oxo-5-PY-6-Q-nicotinonitrile is carried out preferably by heating the reactants in a suitable solvent in the presence of a basic condensing agent. The reaction is conveniently run using an alkali metal lower-alkoxide, preferably sodium methoxide or ethoxide, in dimethylformamide. In practicing the invention, the reaction is carried out in refluxing dimethylformamide using sodium methoxide. Alternatively, methanol and sodium methoxide or ethanol and sodium ethoxide can be used as solvent and basic condensing agent, respectively; however, a longer heating period is required. Other basic condensing agents and solvents include sodium hydride, lithium diethylamide, lithium diisopropylamide, and the like, in an aprotic solvent, e.g., tetrahydrofuran, acetonitrile, ether, benzene, dioxane, and the like.

The following examples will further illustrate the invention without, however, limiting it thereto.

A. 2-HALO-5-PY-6-Q-NICOTINONITRILES

A-1. 2-Chloro-5-(4-pyridinyl)nicotinonitrile—A mixture containing 127 g. of 1,2-dihydro-2-oxo-5-(4-pyridinyl)nicotinonitrile, 800 ml. of phosphorus oxychloride and 12 ml. of dimethylformamide was refluxed for 4 hours, cooled and the excess phosphorous oxychloride and dimethylformamide was distilled off in vacuo. The remaining residue was poured into ice and the aqueous mixture was basified with ammonium hydroxide solution with cooling. The separated product was collected, washed with water, dried, recrystallized from dimethylformamide, washed successively with methanol and ether and vacuum-dried at 60° C. to yield 114 g. of 2-chloro-5-(4-pyridinyl)nicotinonitrile. A 20 g. portion of this product was recrystallized the second time from dimethylformamide, washed successively with methanol and ether and vacuum-dried at 60° C. to yield 16 g. of 2-chloro-5-(4-pyridinyl)nicotinonitrile, m.p., 224°–227° C. with decomposition.

Following the procedure described in Example A-1 but using in place of 1,2-dihydro-2-oxo-5-(4-pyridinyl)nicotinonitrile a molar equivalent quantity of the appropriate 1,2-dihydro-2-oxo-5-PY-nicotinonitrile, it is contemplated that the corresponding 2-chloro-5-PY-nicotinonitriles of Examples A-2 through A-7 can be obtained.

A-2. 2-Chloro-5-(3-pyridinyl)nicotinonitrile.

A-3. 2-Chloro-5-(2-methyl-3-pyridinyl)nicotinonitrile.

A-4. 2-Chloro-5-(5-methyl-3-pyridinyl)nicotinonitrile.

A-5. 2-Chloro-5-(3-ethyl-4-pyridinyl)nicotinonitrile.

A-6. 2-Chloro-5-(2-methyl-4-pyridinyl)nicotinonitrile.

A-7. 2-Chloro-5-(2,6-dimethyl-4-pyridinyl)nicotinonitrile.

Following the procedure described in Example A-1 but using in place of phosphorus oxychloride a molar equivalent quantity of the appropriate halogenating agent, it is contemplated that the designated 2-halo-5-(4-pyridinyl)nicotinonitrile of Examples A-8 or A-9 can be obtained.

A-8. 2-Bromo-5-(4-pyridinyl)nicotinonitrile using phosphorus tribromide or phosphorus oxybromide.

A-9. 2-Chloro-5-(4-pyridinyl)nicotinonitrile using phosphorus trichloride, phosphorus pentachloride or sulfuryl chloride.

Following the procedure described in Example A-1 but using in place of 1,2-dihydro-2-oxo-5-(4-pyridinyl)nicotinonitrile a molar equivalent quantity of the appropriate 1,2-dihydro-2-oxo-5-PY-6-Q-nicotinonitrile, it is contemplated that the corresponding 2-chloro-5-PY-6-Q-nicotinonitriles of Examples A-10 through A-20 can be obtained.

A-10. 2-Chloro-6-methyl-5-(4-pyridinyl)nicotinonitrile.

A-11. 2-Chloro-6-ethyl-5-(4-pyridinyl)nicotinonitrile.

A-12. 2-Chloro-6-methyl-5-(3-pyridinyl)nicotinonitrile.

A-13. 2-Chloro-6-n-propyl-5-(4-pyridinyl)nicotinonitrile.

A-14. 2-Chloro-6-isopropyl-5-(4-pyridinyl)nicotinonitrile.

A-15. 6-n-Butyl-2-chloro-5-(4-pyridinyl)nicotinonitrile.

A-16. 2-Chloro-6-isobutyl-5-(4-pyridinyl)nicotinonitrile.

A-17. 2-Chloro-5-(4-pyridinyl)-6-tert.-butylnicotinonitrile.

A-18. 2-Chloro-6-n-pentyl-5-(4-pyridinyl)nicotinonitrile.

A-19. 6-Ethyl-2-chloro-5-(2-methyl-4-pyridinyl)nicotinonitrile.

A-20. 6-Ethyl-2-chloro-5-(3-pyridinyl)nicotinonitrile.

B. 5-(PY)-6-Q-1H-PYRAZOLO[3,4-b]PYRIDIN-3-AMINES

B-1. 5-(4-Pyridinyl)-1H-pyrazolo[3,4-b]pyridin-3-amine—To a suspension containing 104 g. of 2-chloro-5-(4-pyridinyl)nicotinonitrile in 2 liters of ethanol was added in a rapid stream 100 ml. of 100% hydrazine hydrate. The resulting mixture was refluxed with stirring for 2 hours and then cooled to room temperature. The separated solid was collected, sucked fairly dry on the funnel, dissolved in 750 ml. of hot dimethylformamide and placed in a refrigerator over the weekend. Since the material had crystallized as a very hard mass on the walls of the flask, the mixture was warmed to redissolve the solid. The solution was concentrated in vacuo and the concentrated solution cooled in an ice bath with stirring. The separated solid was collected and the filtrate was concentrated in vacuo to obtain a second crop. The combined crops were slurried with water, collected, dried in vacuo and recrystallized again from dimethylformamide, dried in a vacuum oven at 60° C. for 5 hours to produce 33 g. of 5-(4-pyridinyl)-1H-pyrazolo[3,4-b]pyridin-3-amine, m.p. 291°–293° C.

Following the procedure of Example B-1 but using a molar equivalent quantity of 2-bromo-5-(4-pyridinyl)nicotinonitrile in place of 2-chloro-5-(4-pyridinyl)nicotinonitrile, it is contemplated that 5-(4-pyridinyl)-1H-pyrazolo[3,4-b]pyridin-3-amine can be obtained.

The diacetylderivative of Example B-1 was prepared as a characterizing derivative as follows: A suspension containing 5.3 g. of 5-(4-pyridinyl)-1H-pyrazolo[3,4-b]pyridin-3-amine, 25 ml. of acetic anhydride and a few mg. of p-toluenesulfonic acid was heated with stirring on a steam bath for 2 hours and then allowed to stand overnight at room temperature. About 50 ml. of ether was added to the mixture which was shaken well. The solid was collected, washed with a small amount of fresh ether and air-dried to yield 7.3 g. of solid. The solid was triturated with water and ammonium hydroxide was added until the mixture remained basic. The solid was collected, washed with water and sucked dry. The solid was then recrystallized from 90 ml. of dimethylformamide using decolorizing charcoal and was then washed with ether and dried in a vacuum oven to yield 2.3 g. of N-[1-acetyl-5-(4-pyridinyl)-1H-pyrazolo[3,4-b]pyridin-3-yl]acetamide, m.p. >305° C.

B-2. 1-Methyl-5-(4-pyridinyl)-1H-pyrazolo[3,4-b]pyridin-3-amine—A mixture containing 21.6 g. of 2-chloro-5-(4-pyridinyl)nicotinonitrile, 22 ml. of 1-methylhydrazine and 300 ml. of methanol was refluxed with stirring on a steam bath for 24 hours and then allowed to stand at room temperature overnight. The mixture was cooled well in an ice bath and the golden-yellow solid was collected, washed with ethanol and air-dried to produce 20.8 g. of 1-methyl-5-(4-pyridinyl)-1H-pyrazolo[3,4-b]pyridin-3-amine, m.p. 260°–261° C.

Following the procedure described in Example B-2 but using in place of methylhydrazine a molar equivalent quantity the appropriate 1-R-hydrazine, it is contemplated that the corresponding 1-R-5-(4-pyridinyl)-1H-pyrazolo[3,4-b]pyridin-3-amines of Examples B-3 through B-13 can be obtained.

B-3. 1-Ethyl-5-(4-pyridinyl)-1H-pyrazolo[3,4-b]pyridin-3-amine using 1-ethylhydrazine.

B-4. 1-n-Propyl-5-(4-pyridinyl)-1H-pyrazolo[3,4-b]pyridin-3-amine using 1-n-propylhydrazine.

B-5. 1-Isopropyl-5-(4-pyridinyl)-1H-pyrazolo[3,4-b]pyridin-3-amine using 1-isopropylhydrazine.

B-6. 1-n-Butyl-5-(4-pyridinyl)-1H-pyrazolo[3,4-b]pyridin-3-amine using 1-n-butylhydrazine.

B-7. 1-Isobutyl-5-(4-pyridinyl)-1H-pyrazolo[3,4-b]pyridin-3-amine using 1-isobutylhydrazine.

B-8. 1-(2-Butyl)-5-(4-pyridinyl)-1H-pyrazolo[3,4-b]pyridin-3-amine using 1-(2-butyl)hydrazine.

B-9. 1-(n-Amyl)-5-(4-pyridinyl)-1H-pyrazolo[3,4-b]pyridin-3-amine using 1-(n-amyl)hydrazine.

B-10. 1-(n-Hexyl)-5-(4-pyridinyl)-1H-pyrazolo[3,4-b]pyridin-3-amine using 1-(n-hexyl)hydrazine.

B-11. 1-(2-Ethoxyethyl)-5-(4-pyridinyl)-1H-pyrazolo[3,4-b]pyridin-amine using 1-(2-ethoxyethyl)hydrazine.

B-12. 1-(2-Methoxyethyl)-5-(4-pyridinyl)-1H-pyrazolo[3,4-b]pyridin-3-amine using 1-(2-methoxyethyl)hydrazine.

B-13. 1-(3-Methoxypropyl)-5-(4-pyridinyl)-1H-pyrazolo[3,4-b]pyridin-3-amine using 1-(3-methoxypropyl)hydrazine.

Following the procedure in Example B-1 or B-2 but using in place of 2-chloro-5-(4-pyridinyl)-nicotinonitrile and hydrazine or 1-methylhydrazine, respectively, corresponding molar equivalent quantities of the respective appropriate 2-chloro-5-PY-nicotonitrile and 1-R-hydrazine, it is contemplated that there can be obtained the corresponding 1-R-5-PY-1H-pyrazolo[3,4-b]pyridin-3-amines of Examples B-14 through B-19.

B-14. 1-Methyl-5-(3-pyridinyl)-1H-pyrazolo[3,4-b]pyridin-3-amine.

B-15. 5-(2-Methyl-3-pyridinyl)-1H-pyrazolo[3,4-b]pyridin-3-amine.

B-16. 1-Ethyl-5-(5-methyl-3-pyridinyl)-1H-pyrazolo[3,4-b]pyridin-3-amine.

B-17. 1-Methyl-5-(3-ethyl-4-pyridinyl)-1H-pyrazolo[3,4-b]pyridin-3-amine.

B-18. 1-(2-Methoxyethyl)-5-(2-methyl-4-pyridinyl)-1H-pyrazolo[3,4-b]pyridin-3-amine.

B-19. 1-Methyl-5-(2,6-dimethyl-4-pyridinyl)-1H-pyrazolo[3,4-b]pyridin-3-amine.

B-20. 3-Amino-5-(4-pyridinyl)-1H-pyrazolo[3,4-b]pyridine-1-ethanol—To a suspension containing 33.9 g. of 2-chloro-5-(4-pyridinyl)nicotinonitrile and 650 ml. of methanol was added 55 ml. of 1-(2-hydroxyethyl)hydrazine and the resulting mixture was refluxed with stirring for 24 hours and the mixture then allowed to stand at room temperature overnight. The mixture weas cooled well in an ice bath and the cottony-yellow solid was collected, recrystallized from 1600 ml. of absolute ethanol and the resulting bright yellow solid was dried in a vacuum oven for 5 hours at 90° C. to yield 28.2 g. of 3-amino-5-(4-pyridinyl)-1H-pyrazolo[3,4-b]pyridine-1-ethanol, m.p. 217°-217.5° C.

Following the procedure described in Example B-20 but using in place of 2-chloro-5-(4-pyridinyl)nicotinonitrile and 1-(2-hydroxyethyl)hydrazine corresponding molar equivalent quantities of the appropriate 2-chloro-5-PY-nicotinonitrile and 1-(lower-hydroxyalkyl)-hydrazine, it is contemplated that the 3-amino-5-PY-1H-pyrazolo[3,4-b]pyridine-1-(lower-alkanols) of Examples B-20 through B-26 can be obtained.

B-21. 3-Amino-5-(3-pyridinyl)-1H-pyrazolo[3,4-b]pyridine-1-ethanol.

B-22. 3-Amino-5-(2-methyl-3-pyridinyl)-1H-pyrazolo[3,4-b]pyridine-1-ethanol.

B-23. 3-Amino-5-(5-methyl-3-pyridinyl)-1H-pyrazolo[3,4-b]pyridine-1-n-propanol.

B-24. 3-Amino-5-(4-pyridinyl)-1H-pyrazolo[3,4-b]pyridine-1-(2-propanol), m.p. 208°-209° C.

B-25. 3-Amino-5-(3-ethyl-4-pyridinyl)-1H-pyrazolo[3,4-b]pyridine-1-(2-butanol).

B-26. 3-Amino-5-(2-methyl-4-pyridinyl)-1H-pyrazolo[3,4-b]pyridine-1-ethanol.

B-27. 3-Amino-5-(2,6-dimethyl-4-pyridinyl)-1H-pyrazolo[3,4-b]pyridine-1-ethanol.

Following the procedure described in Example B-20 but using in place of 2-chloro-5-(4-pyridinyl)nicotinonitrile and/or 1-(2-hydroxyethyl)hydrazine molar equivalent quantities of the appropriate 2-chloro-5-PY-6-(lower-alkyl)nicotinonitrile and/or 1-R-hydrazine, respectively, it is contemplated that the corresponding 1-R-5-PY-6-Q-1H-pyrazolo[3,4-b]pyridin-3-amines of Examples B-28 through B-41 can be obtained.

B-28. 1,6-Dimethyl-5-(4-pyridinyl)-1H-pyrazolo[3,4-b]pyridin-3-amine.

B-29. 6-Ethyl-1-methyl-5-(4-pyridinyl)-1H-pyrazolo[3,4-b]pyridin-3-amine.

B-30. 6-Methyl-5-(4-pyridinyl)-1H-pyrazolo[3,4-b]pyridin-3-amine.

B-31. 1-Ethyl-6-methyl-5-(3-pyridinyl)-1H-pyrazolo[3,4-b]pyridin-3-amine.

B-32. 3-Amino-6-methyl-5-(4-pyridinyl)-1H-pyrazolo[3,4-b]pyridine-1-ethanol, m.p. 163°-164° C.

B-33. 3-Amino-6-ethyl-5-(4-pyridinyl)-1H-pyrazolo[3,4-b]pyridine-1-ethanol.

B-34. 1-Methyl-6-n-propyl-5-(4-pyridinyl)-1H-pyrazolo[3,4-b]pyridin-3-amine.

B-35. 6-Isopropyl-5-(4-pyridinyl)-1H-pyrazolo[3,4-b]pyridin-3-amine.

B-36. 6-n-Butyl-1-methyl-5-(4-pyridinyl)-1H-pyrazolo[3,4-b]pyridin-3-amine.

B-37. 3-Amino-6-isobutyl-5-(4-pyridinyl)-1H-pyrazolo[3,4-b]pyridine-1-ethanol.

B-38. 5-(4-Pyridinyl)-6-tert.-butyl-1H-pyrazolo[3,4-b]pyridin-3-amine.

B-39. 1-Methyl-6-n-pentyl-5-(4-pyridinyl)-1H-pyrazolo[3,4-b]pyridin-3-amine.

B-40. 1,6-Diethyl-5-(2-methyl-4-pyridinyl)-1H-pyrazolo[3,4-b]pyridin-3-amine.

B-41. 3-Amino-6-ethyl-5-(3-pyridinyl)-1H-pyrazolo[3,4-b]pyridine-1-ethanol.

B-42. 3-Amino-5-(4-pyridinyl)-1H-pyrazolo[3,4-b]pyridine-1-(2-butanol), m.p. 208.5°-210.5° C.

C. 1-PY-2-(DIMETHYL)ETHENYL LOWER-ALKYL KETONES

C-1. 1-(4-Pyridinyl)-2-(dimethylamino)ethenyl methyl ketone—A mixture containing 20 g. of (4-pyridinyl)-methyl methyl ketone [alternatively named 1-(4-pyridinyl)-2-propanone] and 30 cc. of hexamethylphosphoramide was diluted with 65 cc. of dimethylformamide dimethyl acetal and the resulting mixture was refluxed for 30 minutes. TLC analysis showed a single spot, thereby indicating completion of the reaction (in another run, the reaction appeared to be complete after 30 minutes at room temperature). The reaction mixture was evaporated under reduced pressure using a rotary vaporizer and a pressure of about 0.5 mm., thereby resulting in a crystalline residue weighing 24 g. The residue was decolorized using continuous column chromatography on alumina (about 150 g. of alumina in a 500 cc. continuous separating funnel) using refluxing chloroform. After 1½ hours, the extract was heated in vacuo to remove the chloroform, thereby leaving, as a light yellow crystalline material, 23.2 g. of 1-(4-pyridinyl)-2-(dimethylamino)ethenyl methyl ketone, alternatively named 3-dimethylamino-4-(4-pyridinyl)-3-buten-2-one.

The above preparation can be carried out using in place of hexamethylphosphormamide other solvents, e.g., dimethylformamide, acetonitrile or others noted above; however, hexamethylphosphoramide was conveniently used since (4-pyridinyl)methyl methyl ketone was conveniently prepared as a mixture together with hexamethylphosphoramide, as seen by the following preparation: To a stirred solution containing 70 cc. of freshly distilled diisopropylamine and 200 cc. of tetrahydrofuran at 0° C. under nitrogen was added dropwise over 20 minutes 210 cc. of 2.4 M n-butyllithium in n-hexane and the reaction mixture was stirred for about 35 minutes at about 0°-5° C. To the cold solution was added dropwise over a period of 10 minutes 90 cc. of dry hexamethylphosphoramide (no temperature change) and the resulting light yellow solution was stirred for 15 minutes. To the cold solution at 0° C. was added a solution of 50 cc. of 4-picoline in 150 cc. of dry tetrahydrofuran over a 15 minute period and stirring was continued for 30 minutes at 0° C. Next, a mixture containing 50 cc. of dry ethyl acetate and 150 cc. of tetrahydrofuran was added over a 15 minute period (temperature rose from 0° to about 6° C.) and the resulting mixture was stirred for 20 minutes at 0° C. The ice bath was then removed and stirring continued for another 90 minutes whereupon the temperature of the reaction mixture rose to about 25° C. The reaction mixture was then cooled in an ice bath and to it was added 60 cc. of acetic acid over a period of about 30 minutes. The tetrahydrofuran was distilled off using a rotary vaporizer in vacuo. The remaining mixture was diluted with 400 cc. of water and the aqueous mixture was extracted successively with two 250 cc. portions of isopropyl acetate and three 80 cc. portions of chloroform. The solvents were distilled off under reduced pressure to yield about 137 g. of mixture consisting primarily of the desired product and hexamethylphosphoramide. Another run using the same quantities was carried out as above except after the addition of 60 cc. of glacial acetic acid, the mixture was diluted with only 200 cc. of water, the phases were separated, and the aqueous phase was extracted with five 100 ml. portions of chloroform. The chloroform extract was washed with saline solution and the chloroform was distilled off in vacuo. The remaining mixture of the desired ketone and hexamethylphosphoramide was combined with the above 137 g. of the same mixture and the combined mixture was distilled under reduced pressure to yield the following fractions: I. 63 g., b.p. 110°-112° C. at 4 mm.; II. 59 g. of pale yellow oil, b.p. 113°-115° C. at 3 mm.; and, III. 69 g. of pale yellow oil, b.p. 115°-118° C. at 2.5 mm. Examination of fraction III by NMR showed it to contain a 2:3 mixture by weight of (4-pyridinyl)methyl methyl ketone and hexamethylphosphoramide.

Acid-addition salts of 1-(4-pyridinyl)-2-(dimethylamino)ethenyl methyl ketone are conveniently prepared by adding to a mixture of 5 g. of 1-(4-pyridinyl)-2-(dimethylamino)ethenyl methyl ketone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1-(4-pyridinyl)-2-(dimethylamino)ethenyl methyl ketone and the appropriate acid, e.g., lactic acid or hydrochloric acid, to prepare respectively the monolactate or monohydrochloride salt in aqueous solution.

C-2. 1-(4-Pyridinyl)-2-(dimethylamino)ethenyl ethyl ketone—A mixture containing 87.5 g. of (4-pyridinyl)methyl ethyl ketone [alternatively named 1-(4-pyridinyl)-2-butanone] and 160 cc. of hexamethylphosphoramide was diluted with 100 g. of dimethylformamide dimethyl acetal and the resulting mixture was stirred under nitrogen at room temperature for 45 minutes. The methanol formed by the reaction was distilled off in vacuo using a rotary evaporator and the remaining material was distilled under reduced pressure to yield two fractions, one boiling at 45°-80° C. at 0.5 mm. and the second at 90°-95° C. at 0.5 mm. After TLC analysis showed predominantly only a single spot for each fraction, the two fractions were combined (135 g.) and taken up in 600 ml. of chloroform. The resulting solution was washed with two 300 cc. portions of water and the water was back extracted with three 100 cc. portions of chloroform. The combined chloroform solution was dried over anhydrous sodium sulfate and decolorized by running it through 300 cc. of alumina in a 500 cc. continuous extraction funnel followed by extraction with refluxing chloroform. The chloroform was distilled off in vacuo to yield a red oil which crystallized on standing overnight in an ice bath. The crystalline material was dissolved in carbon tetrachloride, cyclohexane was added and the mixture cooled to yield 64 g. of the resulting yellow crystalline product, 1-(4-pyridinyl)-2-(dimethylamino)ethenyl ethyl ketone. Another 11 g. of crystalline product was obtained by passing the mother liquor through the continuous extraction column and using refluxing chloroform as the solvent.

The above intermediate (4-pyridinyl)methyl ethyl ketone was obtained in a mixture with hexamethylphosphoramide as follows: To a mixture containing 200 cc. of tetrahydrofuran and 70 cc. of diisopropylamine under nitrogen at 0°-5° C. was added 210 cc. of 2.4 N n-butyllithium in n-hexane and the resulting mixture was stirred for 30 minutes. Next was added over 10 minutes period 90 cc. of hexamethylphosphoramide followed by stirring of the mixture for 15 minutes. Then was added over a 15 minute period a solution of 48 cc. of 4-picoline in 150 cc. of tetrahydrofuran followed by stirring for 30 minutes at about 0° C. The ice/acetone bath cooling the reaction mixture was replaced with a dry ice/acetone bath and to the reaction mixture was added over a 20 minute period a mixture of 75 cc. of ethyl propionate in an equal volume of tetrahydrofuran. The reaction mixture was then allowed to warm up to room temperature over a period of about 90 minutes and then was warmed at about 35° C. for 30 minutes. The mixture was next cooled in an ice/acetone bath and to it was added 60 cc. of glacial acetic acid over 30 minutes. The resuling pale yellow suspension was diluted with 200 cc. of water. The mixture was extracted with three 150 cc. portions of ethyl acetate and the ethyl acetate extract was back washed with saline solution. The extract was heated in vacuo to remove the ethyl acetate and the residue was taken up again with ethyl acetate. The solution was washed with water and then heated in vacuo to remove the ethyl acetate followed by heating the residue in vacuo at 50° C. for about 30 minutes to yield 100 g. of pale yellow oil. The pale yellow oil was combined with corresponding samples obtained from two additional runs and then distilled in vacuo to yield 256 g. fraction, b.p. 85°–105° C. at 0.5–1.0 mm. The NMR of this fraction showed it to be a mixture of (4-pyridinyl)methyl ethyl ketone and hexamethylphosphoramide in a respective molar ratio of 1:1.55, that is, 35% or $0.35 \times 256 = 90$ g. of said ketone.

Following the procedure described in Example C-2 but using a molar equivalent quantity of the appropriate PY-methyl lower-alkyl ketone (II) in place of (4-pyridinyl)methyl ethyl ketone, it is contemplated that the corresponding 1-PY-2-(dimethylamino)ethenyl lower-alkyl ketones of Examples C-3 thru C-17 can be obtained.

C-3. 1-(3-Pyridinyl)-2-(dimethylamino)ethenyl methyl ketone using (3-pyridinyl)methyl methyl ketone.

C-4. 1-(4-Pyridinyl)-2-(dimethylamino)ethenyl n-propyl ketone using (4-pyridinyl)methyl n-propyl ketone.

C-5. 1-(4-Pyridinyl)-2-(dimethylamino)ethenyl isopropyl ketone using (4-pyridinyl)methyl isopropyl ketone.

C-6. 1-(4-Pyridinyl)-2-(dimethylamino)ethenyl n-butyl ketone using (4-pyridinyl)methyl n-butyl ketone.

C-7. 1-(4-Pyridinyl)-2-(dimethylamino)ethenyl isobutyl ketone using (4-pyridinyl)methyl isobutyl ketone.

C-8. 1-(4-Pyridinyl)-2-(dimethylamino)ethenyl tert.-butyl ketone using (4-pyridinyl)methyl tert.-butyl ketone.

C-9. 1-(4-Pyridinyl)-2-(dimethylamino)ethenyl n-pentyl ketone using (4-pyridinyl)methyl n-pentyl ketone.

C-10. 1-(2-Methyl-4-pyridinyl)-2-(dimethylamino)ethenyl ethyl ketone using (2-methyl-4-pyridinyl)methyl ethyl ketone.

C-11. 1-(3-Pyridinyl)-2-(dimethylamino)ethenyl ethyl ketone using (3-pyridinyl)methyl ethyl ketone.

D. 1,2-DIHYDRO-6-(LOWER ALKYL)-2-OXO-5-PY-NICOTINONITRILES

D-1. 1,2-Dihydro-6-methyl-2-oxo-5-(4-pyridinyl)-nicotinonitrile, alternatively named 1,6-dihydro-2-methyl-6-oxo-[3,4-b]bipyridine'-5-carbonitrile-To a mixture containing 23 g. of 1-(4-pyridinyl)-2-(dimethylamino)ethenyl methyl ketone and 11 g. of α-cyanoacetamide dissolved in 400 cc. of dimethylformamide was added with stirring 14 g. of sodium methoxide and the resulting reaction mixture was heated in an oil bath under gentle reflux for one hour. TLC analysis showed no starting material in the reaction mixture which was then concentrated in vacuo on a rotary evaporated to a volume of about 80 cc. The concentrate was treated with about 160 cc. of acetonitrile and the resulting mixture was stirred on a rotary evaporator with warming until homogeneous and then cooled. The crystalline product was collected, rinsed successively with acetonitrile and ether, and dried overnight at 55° C. to yield 28 g., of tan crystalline product, namely, sodium salt of 1,2-dihydro-6-methyl-2-oxo-5-(4-pyridinyl)nicotinonitrile, the presence of cyano being confirmed by IR analysis. An 8 g. portion of said sodium salt was dissolved in 75 cc. of hot water, the aqueous solution treated with decolorizing charcoal filtered, the filtrate again treated with decolorizing charcoal and filtered, and the filtrate acidified with 6 N hydrochloric acid by dropwise addition to a pH of 3. The acidic mixture was diluted with ethanol and cooled. The crystalline product was collected, dried, recrystallized from dimethylformamide-water and dried to produce 3.75 g. of 1,2-dihydro-6-methyl-2-oxo-5-(4-pyridinyl)-nicotinonitrile, m.p. 300° C.

Acid-addition salts of 1,2-dihydro-6-methyl-2-oxo-5-(4-pyridinyl)nicotinonitrile are conveniently prepared by adding to a mixture of 2 g. of 1,2-dihydro-6-methyl-2-oxo-5-(4-pyridinyl)nicotinonitrile in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1,2-dihydro-6-methyl-2-oxo-5-(4-pyridinyl)nicotinonitrile and the appropriate acid, e.g., lactic acid or hydrochloric acid, to prepare respectively the monolactate or monohydrochloride salt in aqueous solution.

D-2. 6-Ethyl-1,2-dihydro-2-oxo-5-(4-pyridinyl)-nicotinonitrile, alternatively named 2-ethyl-1,6-dihydro-6-oxo-[3,4'-bipyridine]-5-carbonitrile, m.p. >300° C., 11.6 g., was prepared following the procedure described above in Example D-1 using 20 g. of 1-(4-pyridinyl)-2-(dimethylamino)ethenyl ethyl ketone, 8.4 g. of α-cyanoacetamide, 16.2 g. of sodium methoxide and 250 cc. of dimethylacetamide (as solvent in place of dimethylformamide).

Following the procedure described in Example D-2 but using a molar equivalent quantity of the appropriate 1-PY-2-(dimethylamino)ethenyl lower-alkyl ketone in place of 1-(4-pyridinyl)-2-(dimethylamino)ethenyl ethyl ketone, it is contemplated that the corresponding 1,2-dihydro-2-oxo-5-PY-6-R-nicotinonitriles of Examples D-3 thru D-11 can be obtained.

D-3. 1,2-Dihydro-6-methyl-2-oxo-5-(3-pyridinyl)-nicotinonitrile, using 1-(3-pyridinyl)-2-(dimethylamino)ethenyl methyl ketone.

D-4. 1,2-Dihydro-2-oxo-6-n-propyl-5-(4-pyridinyl)-nicotinonitrile, using 1-(4-pyridinyl)-2-(dimethylamino)ethenyl n-propyl ketone.

D-5. 1,2-Dihydro-6-isopropyl-2-oxo-5-(4-pyridinyl)-nicotinonitrile, using 1-(4-pyridinyl)-2-(dimethylamino)ethenyl isopropyl ketone.

D-6. 6-n-Butyl-1,2-dihydro-2-oxo-5-(4-pyridinyl)-nicotinonitrile, using 1-(4-pyridinyl)-2-(dimethylamino)ethenyl n-butyl ketone.

D-7. 1,2-Dihydro-6-isobutyl-2-oxo-5-(4-pyridinyl)-nicotinonitrile using 1-(4-pyridinyl)-2-(dimethylamino)ethenyl isobutyl ketone.

D-8. 1,2-Dihydro-2-oxo-5-(4-pyridinyl)-6-tert.-butyl-nicotinonitrile, using 1-(4-pyridinyl)-2-(dimethylamino)ethenyl tert.-butyl ketone.

D-9. 1,2-Dihydro-2-oxo-6-n-pentyl-5-(4-pyridinyl)-nicotinonitrile using 1-(4-pyridinyl)-2-(dimethylamino)ethenyl n-pentyl ketone.

D-10. 6-Ethyl-1,2-dihydro-5-(2-methyl-4-pyridinyl)-2-oxonicotinonitrile, using 1-(2-methyl-4-pyridinyl)-2-(dimethylamino)ethenyl ethyl ketone.

D-11. 6-Ethyl-1,2-dihydro-2-oxo-5-(3-pyridinyl)-nicotinonitrile, using 1-(3-pyridinyl)-2-(dimethylamino)ethenyl ethyl ketone.

E. 1-R-3-(NB)-5-PY-6-Q-1H-PYRAZOLO[3,4-b]PYRIDINES

E.1. N,N,1-Trimethyl-5-(4-pyridinyl)-1H-pyrazolo[3,4-b]pyridin-3-amine—A 11.3 g. portion of 1-methyl-5-(4-pyriidnyl)-1H-pyrazolo[3,4-b]pyridin-3-amine was dissolved in 25 ml. of formic acid and the resulting solution was cooled to room temperature. To said solution was added 11.3 ml. of 35% aqueous formaldehyde and the resulting solution was heated on a steam bath for 21 hours. The reaction mixture was evaporated in vacuo to dryness and the remaining red viscous liquid was taken up in 125 ml. of water. To the aqueous mixture was added 100 ml. of 2 N aqueous potassium hydroxide solution and the resulting mixture stirred with warming on a steam bath. After about 5 minutes, a copious yellow solid separated. The mixture was cooled in ice whereupon on standing for about 30 minutes the solid had dissolved to give a faintly turbid solution, which on moderate heating reprecipitated the solid. The solid was collected from the warm mixture, washed with a small quantity of fresh water, recrystallized twice from acetonitrile using 40 ml. and 70 ml. respectively, dried in a vacuum oven at 80° C. to yield 7.2 g. of N,N,1-trimethyl-5-(4-pyridinyl)-1H-pyrazolo[3,4-b]pyridin-3-amine, m.p. 166°–167° C.

E-2. 3-(Dimethylamino)-5-(4-pyridinyl)-1H-pyrazolo[3,2-b]pyridine-1-ethanol was prepared as in Example E-1 using 15.3 g. of 3-amino-5-(4-pyridinyl)-1H-pyrazolo[3,4-b]pyridine-1-ethanol, 30 ml. formic acid, 13.5 ml. of 37% aqueous formaldehyde and a heating period of 17 hours. The dark red reaction solution was evaporated in vacuo and the remaining viscous liquid residue was taken up in about 100 ml. of water. To the aqueous mixture was added 200 ml. of 2 N aqueous potassium hydroxide solution to make the mixture basic and the solution was then heated for 30 minutes on a steam bath. The solution was cooled in an ice bath; the yellow solid that separated was collected, washed with water and air-dried. This product was combined with a 4.2 g. sample of corresponding material obtained in another run starting with 5.1 g. of 3-amino-5-(4-pyridinyl)-1H-pyrazolo[3,4-b]pyridine-1-ethanol, and the combined product was recrystallized from 150 ml. of acetonitrile using decolorizing charcoal and then dried in a vacuum oven at 80° C. to obtain 16 g. of 3-(dimethylamino)-5-(4-pyridinyl)-1H-pyrazolo[3,4-b]pyridine-1-ethanol, m.p. 164°–165° C.

E-3. 3-(Dimethylamino)-α-methyl-5-(4-pyridinyl)-1H-pyrazolo[3,4-b]pyridine-1-ethanol A 13.5 g. sample of 3-amino-α-methyl-5-(4-pyridinyl)-1H-pyrazolo[3,4-b]pyridine-1-ethanol was dissolved in 25 ml. of formic acid and the resulting solution cooled in an ice bath to room temperature. To the solution was added 11.3 ml. of 37% aqueous formaldehyde solution. The resulting reaction mixture was heated on a steam bath with stirring for 22 hours and then evaporated in vacuo to yield a viscous dark red liquid, which was taken up in about 113 ml. of water. To the aqueous solution was added 100 ml. of 2 N aqueous potassium hydroxide solution and the resulting basic solution was stirred while heating on a steam bath for about 45 minutes to hydrolyze any formate ester. The dark solution was cooled in ice whereupon the crystalline product separated. The product was recrystallized from 40 ml. of acetonitrile using decolorizing charcoal and dried to yield 10.3 g. of 3-(dimethylamino)-α-methyl-5-(4-pyridinyl)-1H-pyrazolo[3,4-b]pyridine-1-ethanol, m.p. 117°–118° C.

E-4. N,N-Diethyl-1-methyl-5-(4-pyridinyl)-1H-pyrazolo[3,4-b]pyridin-3-amine A 13.5 g. portion of 1-methyl-5-(4-pyridinyl)-1H-pyrazolo[3,4-b]pyridin-3-amine was mixed with 450 ml. of acetic acid and the mixture warmed with stirring on a steam bath until a clear solution was obtained (about 60° C.). The solution was cooled to about 20° C. and to it was added in small portions with efficient stirring over a period of 55 minutes while maintaining a reaction temperature of 20°–25° C. 22.7 g. of sodium borohydride. The reaction mixture was stirred at room temperature for about 1 hour and then the reaction temperature was raised to about 75° C. whereupon it spontaneously rose to about 86° C., requiring a little cooling. The reaction temperature was then held to about 75° C. for 45 minutes and then allowed to cool to room temperature. The reaction mixture was distilled in vacuo to leave 180.9 g. of viscous orange syrupy material which was dissolved in about 600–700 ml. of warm water. The aqueous mixture was treated with concentrated ammonium hydroxide to a pH of 8.5, requiring about 180 ml. of base, whereupon an oil separated. The mixture was cooled in ice and then extracted with a 500 ml. portion of chloroform followed by a 250 ml. portion of the same solvent. The combined extracts were washed with 200 ml. of water, dried over anhydrous magnesium sulfate and filtered. The filtrate was evaporated in vacuo to yield 17.6 g. of syrupy material which solidified on standing. The solid was recrystallized from 65 ml. of absolute ethanol and dried in a vacuum oven at 70° C. to produce 6.2 g. of N,N-diethyl-1-methyl-5-(4-pyridinyl)-1H-pyrazolo[3,4-b]pyridin-3-amine, m.p. 114°–114.5° C.

E-5. N-[1-(2-Hydroxyethyl)-5-(4-pyridinyl)-1H-pyrazolo[3,4-b]pyridin-3-yl]acetamide To a stirred warm suspension containing 17.9 g. of 3-amino-5-(4-pyridinyl)-1H-pyrazolo[3,4-b]pyridine-1-ethanol and 300 ml. of pyridine was added dropwise with stirring over a period of 9 minutes 7.4 g. of acetic anhydride (97%). The reaction mixture was stirred for 30 minutes without external heat, next stirred for 2½ hours while heating on a steam bath and then allowed to stand overnight at room temperature. The reaction mixture was cooled well in an ice bath and the pale yellow solid that separated was collected, washed with ether and dried in a vacuum oven at 90° C. to yield 7.7 g. of product. This product was combined with corresponding product obtained in another run starting with 2.55 g. of the 3-amino compound and the combined material was recrystallized from 90 ml, of dimethylformamide, washed well with ether and dried in a vacuum oven at 90° C. to produce 6.3 g. of N-[1-(2-hydroxyethyl)-5-(4-pyridinyl)-1H-pyrazolo[3,4-b]pyridin-3-yl]acetamide, m.p. >300° C.

E-6. N-[1-Methyl-5-(4-pyridinyl)-1H-pyrazolo[3,4-b]pyridin-3-yl]acetamide, m.p. 293° C., 13.4 g., was obtained following the procedure described in Example E-5 using 13.5 g. of 1-methyl-5-(4-pyridinyl)-1H-pyrazolo[3,4-b]pyridin-3-amine, 100 ml. of pyridine and 6.8 g. of acetic anhydride.

E-7. N-[1-Methyl-5-(4-pyridinyl)-1H-pyrazolo[3,4-b]pyridin-3-yl]formamide A solution containing 15.8 g. of 1-methyl-5-(4-pyridinyl)-1H-pyrazolo[3,4-b]pyridin-3-amine dissolved in 60 ml. of formic acid (95–97%) was heated with stirring on a steam bath for 18 hours and then allowed to stand at room temperature over the weekend. The reaction mixture was evaporated in vacuo to yield a pale yellow solid. The solid was dissolved in about 300 ml. of water and from the resulting solution there separated almost immediately a yellow solid crystalline material. This solid, identified as A, was collected and the resulting filtrate was treated with concentrated ammonium hydroxide until basic to pH 9 whereupon a solid slowly crystallized. The mixture was cooled in ice and the solid, identified as B, was collected. The solid A was taken up in water and to the aqueous solution was added concentrated ammonium hydroxide solution until the mixture was strongly basic. The solid dissolved almost immediately there separated a copious white precipitate, identified as C, and the mixture was cooled in ice and the solid then collected by filtration. The solid B was recrystallized from 25 ml. of dimethylformamide and the solid C was recrystallized from 90 ml. of dimethylformamide. Both solids were washed with ether and dried in a vacuum oven at 80° C. Both solids B and C were the desired product, N-[1-methyl-5-(4-pyridinyl)-1H-pyrazolo[3,4-b]pyridin-3-yl]formamide. There was obtained 3.0 g. of B, m.p. 248°-249° C. and 11.9 g. of C, m.p. 249°-250° C., thereby providing a total yield of 14.9 g. of N-[1-methyl-5-(4-pyridinyl)-1H-pyrazolo[3,4-b]pyridin-3-yl]formamide.

E-8. N-[1-[2-(Formyloxy)ethyl]-5-(4-pyridinyl)-1H-pyrazolo[3,4-b]pyridin-3-yl]formamide A solution containing 25.5 g. of 3-amino-5-(4-pyridinyl)-1H-pyrazolo[3,4-b]pyridine-1-ethanol and 100 ml. of formic acid (95-97%) was heated on a steam bath with stirring for 18 hours. The reaction mixture was then evaporated in vacuo to dryness to yield an amber colored, viscous liquid residue weighing 39.0 g. TLC examination (75% ethyl acetate-25% methanol) of a sample of this material showed no starting material to be present. The remainder of the reaction mixture was taken up in 600 ml. of water. An insoluble white solid (A) was collected by filtration and the filtrate was made alkaline with ammonium hydroxide to pH of 9 whereupon copious white solid precipitated. This solid (B) was collected by filtration. A portion of solid A was suspended in water and basified with ammonium hydroxide solution. The resulting solid was collected and examined by TLC as above. The solids A and B gave identical TLC's which were identical to the TLC noted hereinabove. The bulk of solid A was suspended in water, basified with ammonium hydroxide solution (only a few drops required) and the resulting solid was collected by filtration. The solids A and B were combined, washed with fresh water and dried in a vacuum oven at 80° C. to yield 30.3 g. of the product, N-[1-[2-(formyloxy)ethyl]-5-(4-pyridinyl)-1H-pyrazolo[3,4-b]pyridin-3-yl]formamide, m.p. 187°-190° C., which is estimated to contain about 10% of unformylated ethanol moiety.

E-9. N-[1-[2-(Acetyloxy)ethyl]-5-(4-pyridinyl)-1H-pyrazolo[3,4-b]pyridin-3-yl]acetamide To a stirred suspension containing 51.1 g. of 3-amino-5-(4-pyridinyl)-1H-pyrazolo[3,4-b]pyridine-1-ethanol and 500 ml. of pyridine was added dropwise over a period of 10 minutes 45 g. of acetic anhydride. The reaction mixture was then heated with stirring on a steam bath whereupon the bright yellow solid dissolved and within a few minutes, a much paler solid began to form. The reaction mixture was heated with stirring for about 2½ hours and then allowed to stand overnight at room temperature. The reaction mixture was cooled well in ice and the resulting pale yellow solid precipitate was collected, washed well with ether and airdried to yield 61.9 g. of N-[1-[2-(acetyloxy)ethyl]-5-(4-pyridinyl)-1H-pyrazolo[3,4-b]pyridin-3-yl]acetamide. A 12 g. sample of this product was recrystallized from 55 ml. of dimethylformamide, washed well with ether and dried in a vacuum oven at 90° C. overnight to yield 11.4 g. of N-[1-[2-(acetoxy)ethyl]-5-(4-pyridinyl)-1H-pyrazolo[3,4-b]pyridin-3-yl]acetamide, m.p. 229°-230° C.

E-10. N-Ethyl-1-methyl-5-(4-pyridinyl)-1H-pyrazolo[3,4-b]pyridin-3-amine To a 3 liter, 3-neck flask equipped with stirrer, condenser and dropping funnel was added 350 ml. of tetrahydrofuran and the reaction system was purged with nitrogen. To the tetrahydrofuran was added with efficient stirring 5.0 g. of lithium aluminum hydride followed by addition of 12.1 g. of N-[1-methyl-5-(4-pyridinyl)-1H-pyrazolo[3,4-b]pyridin-3-yl]acetamide suspended in 1000 ml. of warm tetrahydrofuran. The funnel was rinsed with 50 ml. more of tetrahydrofuran which was added to the reaction mixture, the addition requiring about 28 minutes. The orange reaction mixture was stirred at room temperature for 30 minutes and then refluxed on a steam bath with stirring for 19 hours. To the reaction mixture was carefully added dropwise with stirring and refluxing over a period of 30 minutes 15 ml. of a saturated aqueous solution of sodium potassium tartrate. The reaction mixture was refluxed for 1 additional hour, the hot suspension was filtered and the filter cake was washed with small quantities of fresh tetrahydrofuran. The combined filtrate and washing were evaporated in vacuo to yield 11 g. of yellow solid which was triturated with two 100 ml. of portions of methylene dichloride. The methylene dichloride extract was filtered and the filtrate evaporated to remove the solvent thereby yielding 6.8 g. of material which was recrystallized twice from acetonitrile and once from acetone. There was thus obtained orange crystals which were dried in a vacuum oven at 80° C. for 3 hours to produce 2.2 g. of N-ethyl-1-methyl-5-(4-pyridinyl)-1H-pyrazolo[3,4-b]pyridin-3-amine, m.p. 183°-184° C.

Following the procedure described in Example E-2 or E-4 but using in place of 3-amino-5-(4-pyridinyl)-1H-pyrazolo[3,4-b]pyrdine-1-ethanol or 1-methyl-5-(4-pyridinyl)-1H-pyrazolo[3,4-b]pyridin-3-amine a molar equivalent quantity of the appropriate 1-R-5-PY-6-A-1H-pyrazolo[3,4-b]pyridin-3-amine and, respectively, formic acid and formaldehyde or a molar equivalent quantity of the appropriate lower-alkanoic acid in place of acetic acid, it is contemplated that the corresponding 1-R-3-(NB)-5-PY-6-Q-1H-pyrazolo[3,4-b[pyridines of Examples E-11 through E-26 can be obtained.

E-11. N,N,1-Triethyl-5-(4-pyridinyl)-1H-pyrazolo[3,4-b]pyridin-3-amine using 1-ethyl-5-(4-pyridinyl)-1H-pyrazolo[3,4-b]pyridin-3-amine, acetic acid and sodium borohydride.

E-12. N,N-Dimethyl-1-n-propyl-5-(4-pyridinyl)-1H-pyrazolo[3,4-b]pyridin-3-amine using 1-n-propyl-5-(4-pyridinyl)-1H-pyrazolo[3,4-b]pyridin-3-amine, formic acid and formaldehyde.

E-13. N,N-Diethyl-1-isopropyl-5-(4-pyridinyl)-1H-pyrazolo[3,4-b]pyridin-3-amine using 1-isobutyl-5-(4-pyridinyl)-1H-pyrazolo[3,4-b]pyridin-3-amine, acetic acid and sodium borohydride.

E-14. N,N-Dimethyl-1-n-butyl-5-(4-pyridinyl)-1H-pyrazolo[3,4-b]pyridin-3-amine using 1-n-butyl-5-(4-pyridinyl)-1H-pyrazolo[3,4-b]pyridin-3-amine, formic acid and formaldehyde.

E-15. N,N-Diethyl-1-(n-hexyl)-5-(4-pyridinyl)-1H-pyrazolo[3,4-b]pyridiny-3-amine using 1-(n-hexyl)-5-(4-pyridinyl)-1H-pyrazolo[3,4-b]pyridin-3-amine, acetic acid and sodium borohydride.

E-16. 1-(2-Ethoxyethyl)-N,N-dimethyl-5-(4-pyridinyl)-1H-pyrazolo[3,4-b]pyridin-3-amine using 1-(2-ethoxyethyl)-5-(4-pyridinyl)-1H-pyrazolo[3,4-b]pyridin-3-amine, formic acid and formaldehyde.

E-17. 1-(2-Methoxyethyl)-N,N-di-n-propyl-5-(4-pyridinyl)-1H-pyrazolo[3,4-b]pyridin-3-amine using 1-(2-methoxyethyl)-5-(4-pyridinyl)-1H-pyrazolo[3,4-b]pyridin-3-amine, propionic acid and sodium borohydride.

E-18. N,N,1-Trimethyl-5-(3-pyridinyl)-1H-pyrazolo[3,4-b]pyridin-3-amine using 1-methyl-5-(3-pyridinyl)-1H-pyrazolo[3,4-b]pyridin-3-amine, formic acid and formaldehyde.

E-19. 1-Ethyl-N,N-dimethyl-5-(5-methyl-3-pyridinyl)-1H-pyrazolo[3,4-b]pyridin-3-amine using 1-ethyl-5-(5-methyl-3-pyridinyl)-1H-pyrazolo[3,4-b]pyridin-3-amine, formic acid and formaldehyde.

E-20. N,N-Diethyl-1-methyl-5-(2,6-dimethyl-4-pyridinyl)-1H-pyrazolo[3,4-b]pyridin-3-amine using 1-methyl-5-(2,6-dimethyl-4-pyridinyl)-1H-pyrazolo[3,4-b]pyridin-3-amine, acetic acid and sodium borohydride.

E-21. 3-(Diethylamino)-5-(3-pyridinyl)-1H-pyrazolo[3,4-b]pyridine-1-ethanol using 3-amino-5-(3-pyridinyl)-1H-pyrazolo[3,4-b]pyridine-1-ethanol, acetic acid and sodium borohydride.

E-22. 3-(Dimethylamino)-5-(5-methyl-3-pyridinyl)-1H-pyrazolo[3,4-b]pyridine-1-n-propanol using 3-amino-5-(5-methyl-3-pyridinyl)-1H-pyrazolo[3,4-b]pyridine-1-n-propanol, formic acid and formaldehyde.

E-23. N,N,1,6-Tetramethyl-5-(4-pyridinyl)-1H-pyrazolo[3,4-b]pyridin-3-amine using 1,6-dimethyl-5-(4-pyridinyl)-1H-pyrazolo[3,4-b]pyridin-3-amine, formic acid and formaldehyde.

E-24. N,N,6-Triethyl-1-methyl-5-(4-pyridinyl)-1H-pyrazolo[3,4-b]pyridin-3-amine using 6-ethyl-1-methyl-5-(4-pyridinyl)-1H-pyrazolo[3,4-b]pyridin-3-amine, acetic acid and sodium borohydride.

E-25. 1-Ethyl-6-methyl-N,N-di-n-propyl-5-(3-pyridinyl)-1H-pyrazolo[3,4-b]pyridin-3-amine using 1-ethyl-6-methyl-5-(3-pyridinyl)-1H-pyrazolo[3,4-b]pyridin-3-amine, propanoic acid and sodium borohydride.

E-26. 3-Dimethylamino-6-methyl-5-(4-pyridinyl)-1H-pyrazolo[3,4-b]pyridine-1-ethanol using 3-amino-6-methyl-5-(4-pyridinyl)-1H-pyrazolo[3,4-b]pyridine-1-ethanol, formic acid and formaldehyde.

Following the procedure described in Example E-5 or E-7 using in place of 3-amino-5-(4-pyridinyl)-1H-pyrazolo[3,4-b]pyridine-1-ethanol or 1-methyl-5-(4-pyridinyl)-1H-pyrazolo[3,4-b]pyridine-3-amine a molar equivalent quantity of the appropriate 1-R-5-PY-6-Q-1H-pyrazolo[3,4-b]pyridin-3-amine and a molar equivalent uantrity of the appropriate lower-alkanoic acid anhydride in place of acetic anhydride or formic acid, it is contemplated that the 1-R-3-(NHAc)-5-PY-6-Q-1H-pyrazolo[3,4-b]pyridines of Examples E-27 through E-38 can be obtained.

E-27. N-[1-Ethyl-5-(4-pyridinyl)-1H-pyrazolo[3,4-b]pyridin-3-yl]acetamide using 1-ethyl-5-(4-pyridinyl)-1H-pyrazolo[3,4-b]pyridin-3-amine and acetic anhydride.

E-28. N-[1-n-Butyl-5-(4-pyridinyl)-1H-pyrazolo[3,4-b]pyridin-3-yl]formamide using 1-n-butyl-5-(4-pyridinyl)-1H-pyrazolo[3,4-b]pyridin-3-amine and formic acid.

E-29. N-[1-(2-Methoxyethyl)-5-(4-pyridinyl)-1H-pyrazlo[3,4-b]pyridin-3-yl]propanamide using 1-(2-methoxyethyl)-5-(4-pyridinyl)-1H-pyrazolo[3,4-b]pyridin-3-amine and propanoic acid anhydride.

E-30. N-[1-Methyl-5-(3-pyridinyl)-1H-pyrazolo[3,4-b]pyridin-3-yl]butanamide using 1-methyl-5-(3-pyridinyl)-1H-pyrazolo[3,4-b]pyridin-3-amine and butanoic acid anhydride.

E-31. N-[1-Methyl-5-(3-ethyl-4-pyridinyl)-1H-pyrazolo[3,4-b]pyridin-3-yl]hexanamide using 1-methyl-5-(3-ethyl-4-pyridinyl)-1H-pyrazolo[3,4-b]pyridin-3-amine and hexanoic acid anhydride.

E-32. 2-Methyl-N-[1-methyl-5-(2,6-dimethyl-4-pyridinyl)-1H-pyrazolo[3,4-b]pyridin-3-yl]propanamide using 1-methyl-5-(2,6-dimethyl-4-pyridinyl)-1H-pyrazolo[3,4-b]pyridin-3-amine and 2-methylpropanoic acid anhydride.

E-33. N-[1-(3-Hydroxypropyl)-5-(5-methyl-3-pyridinyl)-1H-pyrazolo[3,4-b]pyridin-3-yl]acetamide using 3-amino-5-(5-methyl-3-pyridinyl)-1H-pyrazolo[3,4-b]pyridine-1-n-propanol and acetic anhydride.

E-34. N-[1-(2-Hydroxypropyl)-5-(4-pyridinyl)-1H-pyrazolo[3,4-b]pyridin-3-yl]formamide using 3-amino-5-(4-pyridinyl)-1H-pyrazolo[3,4-b]pyridine-1-(2-propanol) and formic acid.

E-35. N-[5-(3-Ethyl-4-pyridinyl)-1-(2-hydroxybutyl)-1H-pyrazolo[3,4-b]pyridin-3-yl]formamide using 3-amino-5-(3-ethyl-4-pyridinyl)-1H-pyrazolo[3,4-b]pyridine-1-(2-butanol) and formic acid.

E-36. N-[1,6-Dimethyl-5-(4-pyridinyl)-1H-pyrazolo[3,4-b]pyridin-3-yl]acetamide using 1,6-dimethyl-5-(4-pyridinyl)-1H-pyrazolo[3,4-b]pyridin-3-amine and acetic anhydride.

E-37. N-[6-Ethyl-1-methyl-5-(4-pyridinyl)-1H-pyrazolo[3,4-b]pyridin-3-yl]acetamide using 6-ethyl-1-methyl-5-(4-pyridinyl)-1H-pyrazolo[3,4-b]pyridin-3-amine and acetic anhydride.

E-38. N-[1,6-Diethyl-5-(2-methyl-4-pyridinyl)-1H-pyrazolo[3,4-b]pyridin-3-yl]acetamide using 1,6-diethyl-5-(2-methyl-4-pyridinyl)-1H-pyrazolo[3,4-b]pyridin-3-amine and acetic anhydride.

Following the procedure described in Examples E-8 or E-9 but using in place of 3-amino-5-(4-pyridinyl)-1H-pyrazolo[3,4-b]pyridine-1-ethanol a molar equivalent quantity of the appropriate 3-amino-5-Py-6-Q-1H-pyrazolo[3,4-b]pyridine-1-(lower-alkanol) and either formic acid or a molar equivalent quantity of the appropriate lower-alkanoic acid anhydride in place of acetic anhydride it is contemplated that there can be obtained the corresponding N-[1-(lower-acyloxy)-(lower-alkyl)]-5-PY-6-Q-1H-pyrazolo[3,4-b]pyridin-3-yl]-(lower-alkanamides) of Examples E-39 through E-43.

E-39. N-[1-[2-(Propanoyloxy)ethyl]-5-(4-pyridinyl)-1H-pyrazolo[3,4-b]pyridin-3-yl]propanamide using 3-amino-5-(4-pyridinyl)-1H-pyrazolo[3,4-b]pyridine-1-ethanol and propanoic acid anhydride.

E-40. N-[1-[3-(Acetyloxy)propyl]-5-(5-methyl-3-pyridinyl)-1H-pyrazolo[3,4-b]pyridin-3-yl]acetamide using 3-amino-5-(5-methyl-3-pyridinyl)-1H-pyrazolo[3,4-b]pyridine-1-n-propanol and acetic anhydride.

E-41. N-[1-[2-(Formyloxy)propyl]-5-(4-pyridinyl)-1H-pyrazolo[3,4-b]pyridin-3-yl]formamide using 3-amino-5-(4-pyridinyl)-1H-pyrazolo[3,4-b]pyridine-1-(2-propanol) and formic acid.

E-42. N-[1-[2-(Acetyloxy)ethyl]-6-methyl-5-(4-pyridinyl)-1H-pyrazolo[3,4-b]pyridin-3-yl]acetamide using 3-amino-6-methyl-5-(4-pyridinyl)-1H-pyrazolo[3,4-b]pyridine-1-ethanol and acetic anhydride.

E-43. N-[1-[2-(Acetoxy)ethyl]-6-ethyl-5-(3-pyridinyl)-1H-pyrazolo[3,4-b]pyridin-3-yl]acetamide using 3-amino-6-ethyl-5-(3-pyridinyl)-1H-pyrazolo[3,4-b]pyridine-1-ethanol and acetic anhydride.

Following the procedure described in Example E-10 but using in place of N-[1-methyl-5-(4-pyridinyl)-1H-pyrazolo[3,4-b]pyridin-3-yl]acetamide a molar equivalent quantity of the appropriate N-[1-R-5-PY-6-Q-1H-pyrazolo[3,4-b]pyridin-3-yl]-(lower-alkanamide), it is contemplated that the corresponding N-(lower-alkyl)-1-R-5-PY-6-Q-1H-pyrazolo[3,4-b]pyridin-3-amines of Examples E-44 through E-56 can be obtained.

E-44. N,1-Diethyl-5-(4-pyridinyl)-1H-pyrazolo[3,4-b]pyridin-3-amine using N-[1-ethyl-5-(4-pyridinyl)-1H-pyrazolo[3,4-b]pyridin-3-yl]acetamide.

E-45. 1-n-Butyl-N-methyl-5-(4-pyridinyl)-1H-pyrazolo[3,4-b]pyridin-3-amine using N-[1-n-butyl-5-(4-pyridinyl)-1H-pyrazolo[3,4-b]pyridin-3-yl]formamide.

E-46. 1-(2-Methoxyethyl)-N-n-propyl-5-(4-pyridinyl)-1H-pyrazolo[3,4-b]pyridin-3-amine using N-[1-(2-methoxyethyl)-5-(4-pyridinyl)-1H-pyrazolo[3,4-b]pyridin-3-yl]propanamide.

E-47. N-n-Butyl-1-methyl-5-(3-pyridinyl)-1H-pyrazolo[3,4-b]pyridin-3-amine using N-[1-methyl-5-(3-pyridinyl)-1H-pyrazolo[3,4-b]pyridin-3-yl]butanamide.

E-48. 1-Methyl-5-(3-ethyl-4-pyridinyl)-N-n-hexyl-1H-pyrazolo[3,4-b]pyridin-3-amine using N-[1-methyl-5-(3-ethyl-4-pyridinyl)-1H-pyrazolo[3,4-b]pyridin-3-yl]hexanamide.

E-49. N-Isobutyl-1-methyl-5-(2,6-dimethyl-4-pyridinyl)-1H-pyrazolo[3,4-b]pyridin-3-amine using 2-methyl-N-[1-methyl-5-(2,6-dimethyl-4-pyridinyl)-1H-pyrazolo[3,4-b]pyridin-3-yl]propanamide.

E-50. 3-Ethylamino-5-(5-methyl-3-pyridinyl)-1H-pyrazolo[3,4-b]pyridine-1-n-propanol using N-[1-(3-hydroxypropyl)-5-(5-methyl-3-pyridinyl)-1H-pyrazolo[3,4-b]pyridin-3-yl]acetamide.

E-51. 3-Methylamino-5-(4-pyridinyl)-1H-pyrazolo[3,4-b]pyridine-1-(2-propanol) using N-[1-(2-hydroxypropyl)-5-(4-pyridinyl)-1H-pyrazolo[3,4-b]pyridin-3-yl]formamide.

E-52. 5-(3-Ethyl-4-pyridinyl)-3-methylamino-1H-pyrazolo[3,4-b]pyridin-1-(2-butanol) using N-[5-(3-ethyl-4-pyridinyl)-1-(2-hydroxybutyl)-1H-pyrazolo[3,4-b]pyridin-3-yl]formamide.

E-53. N-Ethyl-1,6-dimethyl-5-(4-pyridinyl)-1H-pyrazolo[3,4-b]pyridin-3-amine using N-[1,6-dimethyl-5-(4-pyridinyl)-1H-pyrazolo[3,4-b]pyridin-3-yl]acetamide.

E-54. N,6-Diethyl-1-methyl-5-(4-pyridinyl)-1H-pyrazolo[3,4-b]pyridin-3-amine using N-[6-ethyl-1-methyl-5-(4-pyridinyl)-1H-pyrazolo[3,4-b]pyridin-3-yl]acetamide.

E-55. N,1,6-Triethyl-5-(2-methyl-4-pyridinyl)-1H-pyrazolo[3,4-b]pyridin-3-amine using N-[1,6-diethyl-5-(2-methyl-4-pyridinyl)-1H-pyrazolo[3,4-b]pyridin-3-yl]acetamide.

E-56. Following the procedure described in Example E-1 but using in place of 1-methyl-5-(4-pyridinyl)-1H-pyrazolo[3,4-b]pyridin-3-amine a molar equivalent quantity of N-ethyl-1-methyl-5-(4-pyridinyl)-1H-pyrazolo[3,4-b]pyridin-3-amine, it is contemplated that there can be obtained N-ethyl-N,1-dimethyl-5-(4-pyridinyl)-1H-pyrazolo[3,4-b]pyridin-3-amine.

E-57. N,N-Di-n-butyl-1-methyl-5-(4-pyridinyl)-1H-pyrazolo[3,4-b]pyridin-3-amine as its monohydrochloride, m.p. 182°-197° C., 5.3 g., was prepared following the procedure described in Example E-4 using 12.5 g. of 1-methyl-5-(4-pyridinyl)-1H-pyrazolo[3,4-b]pyridin-3-amine and 425 ml. of butyric acid.

The usefulness of the compounds of formula I or salts thereof as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of formula I or pharmaceutically-acceptable acid-addition salts thereof at doses of 1, 10, 30, and/or 100 μg/ml., were found to cause significant increases, that is, greater than 25% (cat) or 30% (g. pig) in papillary muscle force and significant increases, that is, greater than 25% (cat) or 30% (g. pig) in right atrial force, while causing a lower percentage increase (about one-half or less than the percentage increase in right atrial force or papillary muscle force) in right atrial rate. Because of the lower control active tensions of guinea pig tissues the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. The compounds of the invention (formula I) have varying degrees of cardiotonic activity. For example, when tested by said guinea pig atria and papillary muscle test procedure, particularly preferred embodiments of Examples E-1, E-2, E-3 and E-10 were found to cause right atrial force and papillary muscle force increases, respectively, of 83% to 106% and 77% to 124% when tested at 3 μg/ml and of 77% to 198% and 172% to 205% at 10 μg/ml.; also, the compounds of Examples E-1, E-2 and E-3 were found to cause respective right atrial force and papillary muscle force increases of 35% to 130% and 42% to 71% when tested at 1 μg/ml. When tested by the same (guinea pig) procedure, preferred embodiments of Examples E-4, E-5, E-6, E-7 and E-8 and the compound of Example E-9 were found to cause respective right atrial force and papillary muscle force increases of 109% to 171% and 57% to 129% when tested at 100 μg/ml; also, preferred embodiments of Examples 6 and 8 were found to cause respective right atrial force and papillary muscle force increases of 53% to 57% and 35% to 70% when tested at 30 μg/ml.

When tested by said anesthetized dog procedure, the compounds of formula I or pharmaceutically-acceptable acid-addition salts thereof at doses 0.03, 0.1, 0.3 and/or 1.0 mg/kg. administered intravenously were found to cause significant increases, that is, 25% or greater, in cardiac contractile force or cardiac contractility with lower changes in heart rate and blood pressure. For example, when tested at one or more of said dose levels by this procedure, the compounds of Examples E-1 and E-2 were found to cause increases of 30 to 200% in contractile force and lower changes in heart rate and blood pressure. Similarly, the compound of Example E-1 when administered intraduodenally to the anesthetized dog at 1.0 and 3.0 mg./kg. was found to cause cardiac contractility increases of 55% and 107% respectively with only low changes in heart rate and blood pressure.

The present invention includes within its scope a cardiotonic composition for increasing cardiac contractility, said composition comprising a pharmaceutically-acceptable carrier and, as the active component thereof, a cardiotonically-effective amount of 1-R-3-(NB)-5-PY-6-Q-1H-pyrazolo[3,4-b]pyridine (formula 1) or pharmaceutically-acceptable acid-addition salt thereof. The invention also includes within its scope the method for increasing cardiac contractility in a patient requiring such treatment which comprises administering to such patient said cardiotonic composition containing a cardiotonically-effective amount of said 1-R-3-(NB)-5-PY-6-Q-1H-pyrazolo[3,4-b]pyridine (formula I) or pharmaceutically-acceptable acid-addition salt thereof. In clinical practice said compound or salt thereof will normally be administered orally or prenterally in a wide variety of dosage forms.

Solid compositions for oral administration include compressed tablets, pill, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspension, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or exicpients.

Preparations according to the invention for parenteral administration include sterile aqueous, aqueous-organic, and organic solutions, suspensions and emulsions. Exmaples of organic solvents or suspending media are propylene glycol, polyethylene glycol, vegetable oils such as olive oil and injectable organic esters such as ethyl oleate. These compositions can also contain adjuvants such as stabilizing, perserving, wetting, emulsifying and dispersing agents.

They can be sterilized, for example by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A 1-R-3-(NB)-5-PY-6-Q-1H-pyrazolo[3,4-b]pyridine having the formula

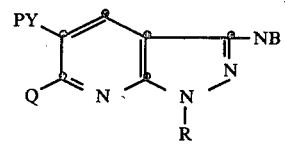

where R is lower-alkyl, lower-hydroxyalkyl, lower-acyloxy-(lower-alkyl) or lower-alkoxyalkyl, Q is hydrogen or lower-alkyl, PY is 4- or 3-pyridinyl or 4- or 3-pyridinyl having one or two lower-alkyl substituents, and NB is selected from $NHR_1$, $NR_1R_2$, or NHAc where $R_1$ and $R_2$ are each lower-alkyl and Ac is lower-acyl, or pharmaceutically-acceptable acid-addition salts thereof.

2. A compound according to claim 1 where R is methyl, ethyl, 2-hydroxyethyl or 2-hydroxypropyl.

3. A compound according to claim 1 where NB is $NHCH_3$, $NHC_2H_5$, $N(CH_3)_2$, NHCHO or $NHCOCH_3$.

4. A compound according to claim 1 where PY is 4-pyridinyl or 3-pyridinyl.

5. N,N,1-Trimethyl-5-(4-pyridinyl)-1H-pyrazolo[3,4-b]pyridin-3-amine according to claim 1 where R is methyl, Q is hydrogen, PY is 4-pyridinyl and NB is $N(CH_3)_2$.

6. 3-(Dimethylamino)-5-(4-pyridinyl)-1H-pyrazolo[3,4-b]pyridine-1-ethanol according to claim 1 where R is 2-hydroxyethyl, Q is hydrogen, PY is 4-pyridinyl and NB is $N(CH_3)_2$.

7. 3-(Dimethylamino)-α-methyl-5-(4-pyridinyl)-1H-pyrazolo[3,4-b]pyridine-1-ethanol according to claim 1 where R is 2-hydroxypropyl, Q is hydrogen, PY is 4-pyridinyl and NB is $N(CH_3)_2$.

8. N-Ethyl-1-methyl-5-(4-pyridinyl)-1H-pyrazolo[3,4-b]pyridin-3-amine according to claim 1 where R is methyl, Q is hydrogen, PY is 4-pyridinyl and NB is $NHC_2H_5$.

9. N-[1-[2-(Formyloxy)ethyl]-5-(4-pyridinyl)-1H-pyrazolo[3,4-b]pyridin-3-yl]formamide according to claim 1 where R is 2-formyloxyethyl, Q is hydrogen, PY is 4-pyridinyl and NB is NHCHO.

10. N-[1-[2-(Acetyloxy)ethyl]-5-(4-pyridinyl)-1H-pyrazolo[3,4-b]pyridin-3-yl]acetamide according to claim 1 where R is 2-acetyloxyethyl, Q is hydrogen, PY is 4-pyridinyl and NB is $NHCOCH_3$.

11. A cardiotonic composition for increasing cardiac contractility, said composition comprising a pharmaceutically-acceptable inert carrier and, as the active component thereof, a cardiotonically-effective amount of 1-R-3-(NB)-5-PY-6-Q-1H-pyrazolo[3,4-b]pyridine or pharmaceutically-acceptable acid-addition salt thereof, where R is lower-alkyl, lower-hydroxyalkyl, lower-acyloxy-(lower-alkyl) or lower-alkoxyalkyl, Q is hydrogen or lower-alkyl, PY is 4- or 3-pyridinyl or 4- or 3-pyridinyl having one or two lower-alkyl substituents, and NB is selected from $NHR_1$, $NR_1R_2$ or NHAc where $R_1$ and $R_2$ are each lower-alkyl and Ac is lower-acyl.

12. A composition according to claim 11, where PY is 4-pyridinyl or 3-pyridinyl, R is methyl, ethyl, 2-hydroxyethyl, 2-hydroxypropyl, 2-formyloxyethyl or 2- acetyloxyethyl, Q is hydrogen or methyl and NB is NHCH$_3$, NHC$_2$H$_5$, N(CH$_3$)$_2$, NHCHO or NHCOCH$_3$.

13. The method for increasing cardiac contractility in a patient requiring such treatment which comprises administering orally or parenterally in a solid or liquid dosage form to such patient said cardiotonic composition of claim 11.

14. The method for increasing cardiac contractility in a patient requiring such treatment which comprises administering orally or parenterally in a solid or liquid dosage form to such patient said cardiotonic composition of claim 12.

* * * * *